(12) United States Patent
Kühne (10) Patent No.: US 11,608,487 B2
(45) Date of Patent: Mar. 21, 2023

(54) FLUID SUPPLY INTERFACE HAVING A SAFETY VALVE FOR A CELL CULTURE SYSTEM, USE OF SUCH A FLUID SUPPLY INTERFACE FOR MANAGING CELL CULTURE CONTAINERS, AND CELL CULTURE MANAGEMENT SYSTEM

(71) Applicant: Hamilton Bonaduz AG, Bonaduz (CH)

(72) Inventor: Oliver Kühne, Malans (CH)

(73) Assignee: Hamilton Bonaduz AG, Bonaduz (CH)

( * ) Notice: Subject to any disclaimer, the term of this patent is extended or adjusted under 35 U.S.C. 154(b) by 989 days.

(21) Appl. No.: 16/310,656

(22) PCT Filed: Jun. 14, 2017

(86) PCT No.: PCT/EP2017/064564
§ 371 (c)(1),
(2) Date: Dec. 17, 2018

(87) PCT Pub. No.: WO2017/216234
PCT Pub. Date: Dec. 21, 2017

(65) Prior Publication Data
US 2020/0032195 A1    Jan. 30, 2020

(30) Foreign Application Priority Data

Jun. 17, 2016 (DE) ..................... 10 2016 210 851.4

(51) Int. Cl.
*C12M 1/00* (2006.01)
*C12M 1/34* (2006.01)

(52) U.S. Cl.
CPC ............ *C12M 41/40* (2013.01); *C12M 23/40* (2013.01); *C12M 29/00* (2013.01)

(58) Field of Classification Search
CPC ...... C12M 41/40; C12M 23/40; C12M 29/00; C12M 33/07; C12M 41/00
(Continued)

(56) References Cited

U.S. PATENT DOCUMENTS 4,349,042 A * 9/1982 Shimizu ................ F16K 31/084
137/39
5,605,173 A * 2/1997 Arnaud ................... F16K 11/24
137/597
(Continued)

FOREIGN PATENT DOCUMENTS

DE          42 07 346     9/1993
DE    10 2004 032 236.8    1/2006
(Continued)

OTHER PUBLICATIONS

Jager et al., "English machine translation of DE 10-2013-201069". Translated on Aug. 23, 2021.*
(Continued)

*Primary Examiner* — Liban M Hassan
(74) *Attorney, Agent, or Firm* — Tollefson IP (57) ABSTRACT

A fluid supply interface includes at least one supply coupling configuration, at least one discharge coupling configuration, at least one user coupling configuration, and a fluid conduit that connects the supply, discharge, and user coupling configurations to one another. A supply valve is capable of having fluid flow through it or is blocked for flow through it. A discharge valve is capable of having fluid flow through it or is blocked for flow through it. The supply valve is preloaded into a blocking position that prevents flow, and opens by means of a sufficiently large pressure difference between the two sides of the supply valve, against the preload force, for flow through in a direction from the supply coupling configuration toward the fluid conduit. The discharge valve likewise being preloaded into a closed position that prevents flow through it.

18 Claims, 5 Drawing Sheets

(58) Field of Classification Search
USPC .................................................. 435/289.1
See application file for complete search history.

(56) References Cited

U.S. PATENT DOCUMENTS

| | | | |
|---|---|---|---|
| 8,778,281 B2* | 7/2014 | Holenstein | G01N 35/1065 422/509 |
| 10,093,893 B2* | 10/2018 | Jager | C12M 33/07 |
| 2003/0040116 A1 | 2/2003 | Canos et al. | |
| 2005/0173019 A1* | 8/2005 | Navarro | B65B 3/30 141/91 |
| 2010/0206388 A1* | 8/2010 | Bielab | F16K 31/0644 137/12 |
| 2016/0186124 A1 | 6/2016 | Jäger et al. | |
| 2017/0198247 A1 | 7/2017 | Seiler et al. | |

FOREIGN PATENT DOCUMENTS

| | | |
|---|---|---|
| DE | 10 2013 201 069 | 7/2014 |
| DE | 10 2014 214 076 | 1/2016 |
| EP | 1273919 | 1/2003 |

OTHER PUBLICATIONS

Search Report Issued in DE 10 2016 210 851.4 dated Mar. 14, 2017.
International Search Report Issued in PCT/EP2017/064564 dated Sep. 20, 2017.
Will, et al., "Hydraulik—Grundlagen Komponenten," Schaltungen, 4th Ed., 2008, pp. 204-208.

* cited by examiner

FLUID SUPPLY INTERFACE HAVING A SAFETY VALVE FOR A CELL CULTURE SYSTEM, USE OF SUCH A FLUID SUPPLY INTERFACE FOR MANAGING CELL CULTURE CONTAINERS, AND CELL CULTURE MANAGEMENT SYSTEM

CROSS REFERENCE TO RELATED APPLICATIONS

This application is the National Stage of International Application No. PCT/EP2017/064564, filed on Jun. 14, 2017, which claims priority to German Application No. 10 2016 210 851.4, filed on Jun. 17, 2016. The contents of both applications are hereby incorporated by reference in their entirety.

The present invention relates to a fluid supply interface for a cell culture system, the fluid supply interface comprising:
- at least one supply coupling configuration for coupling a respective supply fluid line onto the fluid supply interface;
- at least one discharge coupling configuration for coupling a respective discharge fluid line, different from the supply fluid line, onto the fluid supply interface;
- at least one user coupling configuration for coupling a respective user fluid line, different from the supply fluid line and the discharge fluid line, onto the fluid supply interface;
- a fluid conduit that connects the at least one supply coupling configuration, the at least one discharge coupling configuration, and the at least one user coupling configuration to one another;
- at least one supply valve by means of which, depending on its position, a supply coupling configuration is capable of having fluid flow through it or is blocked for flow through it;
- at least one discharge valve, different from the supply valve, by means of which, depending on its position, a discharge coupling configuration is capable of having fluid flow through it or is blocked for flow through it, the at least one supply valve being preloaded, preferably by magnetic force, into a blocking position that prevents flow, and opening by means of a sufficiently large pressure difference between the two sides of the supply valve, against the, preferably magnetic, preload force, for flow through in a direction from the supply coupling configuration toward the fluid conduit, the at least one discharge valve likewise being preloaded into a closed position that prevents flow through it.

A fluid supply interface of this kind is known from DE 10 2013 201 069 A1. It serves to manage a plurality of cell culture containers, i.e. supply them with nutrient media, discharge exhausted media, clean the cell culture containers as applicable, and harvest cells from a completely cultured cell culture at the end of a culturing cycle. The fluid supply interface enables different cell culture containers to be coupled successively to the user coupling configuration, so that a plurality of cell culture containers can be managed with a single fluid supply interface. The layout and structure of the fluid supply interface prevent cross-contamination between the various cell culture containers.

On the known fluid supply interface, all the valves used therein of a coupling configuration embodied at the supply interface open by lifting a valve body toward the user coupling configuration. In some circumstances, in the context of pressure-induced forced opening of a supply valve, fluid can thereby be conveyed from a supply fluid line to the user coupling configuration. But if, as a result of a malfunction of a delivery pump of the supply fluid line, the latter happens to be continuously under pressure, or if, due to a malfunction of the supply valve or discharge valve or of a switching device for actuation thereof, the supply valve happens not to close and the discharge valve not to open, an undesired rise in the pressure of the fluid contained in the fluid conduit can occur therein. The fluid supply interface can thereby be damaged. Fluid can then furthermore, in some circumstances, emerge out of the interface in uncontrolled fashion at gap surfaces that can exist between the user coupling configuration and a counterpart user coupling configuration, coupled thereonto, of a cell culture container.

The object of the present invention is therefore to make the fluid supply interface recited previously even more operationally reliable.

This object is achieved according to the present invention by a fluid supply interface of the species in which at least one discharge valve, constituting a safety valve, is embodied to open upon exceedance of a predetermined pressure difference between the two sides of the safety valve, against its preload force, for flow through in a direction away from the fluid conduit and toward the discharge coupling configuration.

Thanks to the aforesaid embodiment of the discharge valve as a safety valve, upon exceedance of the predetermined pressure difference it can open, driven by the overpressure and irrespective of a switch operation, initiated via a switching device, for deliberate modification of its operating position, and can thereby reduce an overpressure that has occurred in the fluid conduit. Fluid can flow through the discharge valve thereby opened, out of the fluid conduit to the discharge coupling configuration and thus to a discharge fluid line.

In principle, the physical construction of the safety valve is immaterial provided it opens at the predetermined pressure difference.

The pressure difference can be predetermined by way of the physical conformation of the discharge valve embodied as a safety valve, for example by deliberately setting a preload force necessary for opening of the discharge valve. This can be achieved, for example, by the fact that a preload device acting on a valve body of the discharge valve in a direction toward its closed position is dimensioned in terms of design in accordance with the desired opening force. Assuming known dimensions of the discharge valve, a desired opening force can be equal to a predetermined pressure difference between its two sides when the area in the valve on which the opening force acts is known.

The aforesaid "two sides" of a valve are one side in a flow direction before a valve body, and one side in a flow direction after the valve body.

Preferably the lifting direction of the valve body of the discharge valve, embodied as a safety valve, off a valve seat for overpressure-induced opening corresponds to the flow direction, desired for overpressure reduction, of the fluid away from the fluid conduit. The valve body of the safety valve is therefore preferably, in its closed position, at a smaller spacing from the fluid conduit or from the user coupling configuration than in its flowthrough position in which flow can occur through the safety valve in a direction away from the fluid conduit.

Because the fluid supply interface presented here serves preferably for management of cell culture containers of a cell culture system, a corresponding at least locally complementary counterpart user coupling configuration of a cell culture container is temporarily coupled onto the user coupling configuration. The counterpart user coupling configuration is connected to the cell culture container via a user fluid line. The fluid conduit that connects to one another the coupling configurations of the fluid supply interface which are recited in the present Application can thus serve as a reference point for describing flows through the supply interface. If the fluid conduit has too large a physical extent to serve in an individual case as a usable reference point, the at least one user coupling configuration can serve as a reference point. If several user coupling configurations are provided, for example because more than one counterpart user coupling configuration is embodied on each cell culture container, then one of the plurality of user coupling configurations can arbitrarily be selected; all that needs to be kept in mind is that the same user coupling configuration of the fluid supply interface is always utilized within one assessment instance.

Thus while the at least one user coupling configuration is embodied as operationally intended for only temporary coupling of a counterpart user coupling configuration, the at least one supply coupling configuration and the at least one discharge coupling configuration are preferably embodied for permanent coupling respectively of a supply fluid line or discharge fluid line. The embodiment for "permanent" coupling is not to be understood to mean, for example, that the respective fluid line can be detached only destructively from its coupling configuration. The coupling of a fluid line onto the coupling configuration is already "permanent" for purposes of the present invention when it can be released from the coupling configuration for repair and maintenance purposes but remains permanently connected to the supply interface during operation of the supply interface as intended, whereas the user coupling configuration is coupled several times to counterpart user coupling configurations of different cell culture containers.

The supply coupling configuration and/or discharge coupling configuration can be constituted, for example, by tube fittings onto which the end of a hose or tube can be slid, and which can be secured by suitable securing means, for example hose clamps and the like, against being pulled off. The aforementioned coupling configurations can also be constituted, however, by hose coupling components or tube coupling components of which one is provided respectively on the supply coupling configuration or discharge coupling configuration and the respective other on the associated fluid line, so that they can be connected to one another to form a continuous fluid line.

In the context of a simple but flexible design of the fluid supply interface, the fluid conduit can be constituted by a hose into which the lines coupled to the at least one supply coupling configuration and the at least one discharge coupling configuration connect.

Because the fluid supply interface is preferably movable to different coupling locations by means of a handling device, for example a multi-axis robot, for coupling onto different cell culture containers, it is preferred if the fluid conduit and thus the fluid supply interface are embodied to be as stiff as possible. The fluid supply interface therefore preferably has a substantially rigid housing in which the fluid conduit is embodied. The user coupling configuration can preferably be embodied integrally on the housing.

The at least one supply coupling configuration and/or the at least one discharge coupling configuration can be embodied integrally with the housing or can be installed, as configuration subassemblies, in corresponding receptacles on the housing. The latter is preferred in the interest of simpler fabrication of the fluid supply interface. At least some of, preferably all, the supply valves and/or discharge valves are preferably located in the housing.

The housing can be embodied in multiple parts, for example in order to implement complex housing shapes. Preferably, however, the housing is embodied in one piece.

Although in principle the fluid conduit can take any desired course in the fluid supply interface and in particular in its housing, a fluid conduit having a straight-line course, at least having a straight-line course between the supply coupling configuration provided farthest from the at least one user coupling configuration and the discharge coupling configuration provided farthest from that same at least user coupling configuration, is advantageous for the fluid supply interface according to the present invention.

The fluid conduit is therefore either embodied as a straight-line blind hole in the housing of the fluid supply interface which at its opening end is preferably closed off by a stopper or the like or is closable by a valve, or is embodied by a passthrough hole, passing through the housing, which can be closed off, or closable by a valve, at both longitudinal ends in the housing. Both the blind hole and the passthrough opening can be embodied simply in terms of production engineering, and therefore advantageously, as bores.

Preferably the at least one supply coupling configuration and the at least one discharge coupling configuration are provided along the fluid conduit on different sides of the at least one user coupling configuration, in order to prevent a fluid-mechanical join between a supply coupling configuration and discharge coupling configuration in which the fluid flowing between those coupling configurations does not reach the user coupling configuration. The at least one supply coupling configuration and the at least one discharge coupling configuration are therefore preferably arranged in the fluid supply interface in such a way that a fluid flow existing or being produced between them in the fluid conduit always flows past the user coupling configuration.

The predetermined overpressure necessary for opening the discharge valve embodied as a safety valve is qualitatively an overpressure situation in which the magnitude of the pressure on that side of the valve body of the safety valve which is located closer to the fluid conduit is greater than on that side of the valve which is located remotely from the fluid conduit when the lifting direction of the valve body on the safety valve that is described above as preferred is implemented.

In principle, the discharge valve embodied as a safety valve, like the at least one supply valve, can comprise a magnetic preload device. The magnetic force proceeding from a magnet decreases approximately as the square of the distance from the magnet, however, so that the return force becomes progressively less with increasing distance of a valve body from the preload device. The safety valve therefore preferably comprises a mechanical preload device, which can enable even a long lifting travel of a valve body off its valve seat and thus a large opening cross section of the safety valve in the flowthrough position. An overpressure undesirably occurring in the fluid conduit can thus be reduced very quickly. The mechanical preload device can be, for example, an elastomeric compression body that, upon lifting of the valve body off its valve seat, becomes compressed against its elasticity inherent in the material. The mechanical preload device preferably encompasses a metal spring, particularly preferably a helical compression spring, which can be adjusted very precisely to a predetermined opening force based on material selection and spring wire cross section. Because the helical compression spring preferably exhibits a Hooke spring characteristic in its working range as intended in the discharge valve, a return force whose magnitude increases with an increasing lifting travel of the valve body off the valve seat can be effected. Reliable return of the valve body of the safety valve into the closed position is thereby ensured.

The fastest possible reduction of an undesired overpressure is not important in the context of the at least one supply valve, and for that reason the use therein of magnetic preload devices to ensure excellent operating hygiene, preferably utilizing annular preload magnets through which the respective fluid line cavity passes, is more greatly preferred than in the safety valve. The at least one supply valve is therefore preloaded magnetically into its blocking position.

In order to protect the preload magnet of a supply valve and/or discharge valve, preloaded into its blocking or closed position, from repeated placement of the valve body, the valve seat is preferably arranged between the valve body and preload magnet.

Irrespective of whether the at least one discharge valve, in particular the safety valve, is preloaded into the closed position by a magnetic or mechanical preloading device or by an elastomeric or a metallic spring device, it is advantageous in terms of achieving noncontact (and therefore high-purity) actuation of the at least one discharge valve, in particular the safety valve, if it is switchable between its operating positions (closed position and flowthrough position) by modification of an external magnetic field. The magnetic field that can be applied to the discharge valve from outside, and the preload device of the discharge valve, must then be coordinated with one another in such a way that the force exerted by the external magnetic field on the at least one discharge valve can overcome the preload force into the closed position. The use of helical compression springs as a mechanical preload device of the discharge valve is advantageous for this coordination as well. In principle, however, the safety valve can also be openable only by way of the aforesaid pressure difference.

The at least one discharge valve can comprise a displaceable actuation member that is displaced by the external magnetic field and itself in turn, upon its displacement, moves a valve body of the discharge valve from the closed position into the flowthrough position. In the interest of a minimum number of components required to constitute the discharge valve, however, it is advantageous if the discharge valve comprises a valve body having or made of ferromagnetic and/or permanently magnetized material. The external magnetic field can then act directly on the valve body and move it between its operating positions.

The same applies to the supply valve. It too is preferably switchable between its operating positions (blocking position and passthrough position), irrespective of the configuration of the discharge valve, by modification of an external magnetic field, so that a desired operating position can be deliberately established from outside. The supply valve as well therefore preferably comprises, for the reasons recited above, a valve body having or made of ferromagnetic and/or permanently magnetized material.

As a result of the aforementioned switchability of the at least one discharge valve and/or the at least one supply valve by modification of an external magnetic field, the respective valve can be, for example, switched manually into a desired operating position independently of a switching device that switches the valves.

The modification of an external magnetic field can be brought about by modifying a current-flow state of an electromagnet arranged sufficiently close to the respective valve, or by bringing a permanent magnet closer to and farther from the valve. The use of a permanent magnet that can be brought closer and farther is preferred over use of an electromagnet, since even when current flows through the electromagnet it can constitute a source of heat, which is undesirable when thermally sensitive fluids or thermally sensitive cells are being used.

In order to facilitate dimensioning of the valves, their preload devices, and any external magnetic-field sources, it is preferred if the at least one discharge valve and the at least one supply valve comprise the same valve bodies. The valve bodies are preferably spherical, i.e. ball-shaped, so that their orientation relative to their surroundings in the fluid supply interface is immaterial.

To prevent a valve body, when it is lifted off its valve seat of the respective valve, from being detached by the fluid flow that is then permitted and/or from moving under the force of gravity out of the influence region of its preload device so that it can no longer be returned into the blocking position, it is advantageous if a retaining configuration is embodied on the fluid supply interface, which configuration, when a valve body is lifted off the valve seat, retains a valve body of the supply valve in its passthrough position in the influence region of the (preferably magnetic) preload force exerted on the valve body. The retaining configuration is preferably embodied in the fluid conduit, so that the valve body of the supply valve preferably lifts off its valve seat into the fluid conduit.

The retaining configuration is preferably embodied as a wall configuration, in particular a concave, for example negatively dome-shaped, wall configuration, of the fluid conduit, so that no separate components are required for it. The wall configuration can be generated, for example, by material-removing machining of a housing portion that constitutes the fluid conduit in the region of the respectively relevant valve. The retaining configuration can extend in portions, orthogonally to the direction in which the fluid conduit proceeds in the region of the respective valve, into the material that defines the fluid conduit. An end milling cutter and/or cylindrical cutter, in particular a ball cutter, can be used, for example, for material-removing manufacture of a wall configuration in the fluid conduit constituting a retaining configuration for the valve body of a supply valve.

The valve body of the at least one supply valve preferably already extends into the fluid conduit when the at least one supply valve is in the blocking position, but preferably over no more than half its dimension in a direction orthogonal to the course of the fluid conduit. What can be achieved thereby is that a flow occurs in the valve conduit around the valve body, but does not detach it.

It is also preferred if the valve body of a supply valve travels over a lifting distance, between its blocking position and its position maximally lifted off from the valve, that is less than its largest extent in a lifting direction, more preferably less than two-thirds of its extent in a lifting direction. Particularly preferably, the valve body travels by no more than half its greatest extent in a lifting direction between its blocking position in which it abuts against a valve seat and its maximally lifted position. In the context of the preferred use of a spherical valve body, the maximum dimension of the valve body in any direction is always the diameter thereof.

For clarification, the fluid conduit is always to be conceived of, at the connection points of fluid lines that connect into the fluid conduit, as continuing beyond the connection point in accordance with its embodiment on one or both sides of the connection point, for determination of the protrusion depth into the fluid conduit of the valve body that, in the blocking position, is usually still located in the connecting fluid line.

In addition, undesired detachment of a valve body from its valve can be prevented by the fact that the flow cross section of the fluid conduit in a portion adjacent to the retaining configuration is smaller than a cross-sectional dimension of the valve body orthogonally to the path along which the fluid conduit proceeds in the adjacent portion, so that penetration of the valve body into the fluid conduit is prevented.

In order to allow the linear stroke of the valve body out of the closed or blocking position, i.e. away from the valve seat, to be limited without additional components, it is advantageous if the fluid conduit encloses an angle, preferably a right angle, with the lifting direction of the valve body of at least one supply valve and/or of at least one discharge valve. In this case a wall portion of the fluid conduit, in particular a wall portion embodied as described above as a retaining configuration of the fluid conduit, can serve together with the valve seat to limit the movement stroke of the valve body between its operating positions.

When an "operating position" (blocking position or pass-through position) of the valve body is discussed in this Application, this is synonymous with the operating position of the supply valve itself. The same applies to the operating positions of the valve body of the discharge valve and the operating positions of the discharge valve.

The management of cell culture containers usually requires deliberate delivery of more than one fluid to a respectively coupled-on cell culture container and thus to the fluid supply interface, and provision is therefore made that the fluid supply interface comprises a plurality of supply coupling configurations, which are connected to one another by the fluid conduit, and each comprise a supply valve that is preloaded, preferably by magnetic force, into a blocking position that prevents flow, and as a result of a sufficiently large pressure difference between the two sides of the supply valve, opens against the preferably magnetic preload force for flow through in a direction from the respective supply coupling configuration toward the fluid conduit.

The fluid supply interface preferably comprises a switching device having at least one magnet, also referred to below as a "switching magnet," with which, at a supply switching location, an external magnetic field generated by the at least one magnet is modifiable so that a supply valve provided at the supply switching location can be switched deliberately between its operating positions. Thanks to the switching device, at least some of the supply valves that are provided can be switched between their respective operating positions in noncontact fashion, which minimizes or indeed excludes the risk of impairment, due to the switching device, of the quality of the fluids conveyed through the supply valves.

The present invention is intended also to encompass a fluid supply interface, having a plurality of supply coupling configurations connected to one another by means of the fluid conduit, each having a supply valve embodied as described above, having no switching device. This is not preferred, however, since it is advantageous if at least some of the supply valves are switchable deliberately between their operating positions irrespective of the fluid pressure and fluid pressure difference existing at the respective valve location.

In order to reduce the complexity of the supply interface and of the constituents necessary in order to construct it, provision is preferably made that not all the supply valves that are present are switchable by way of the switching device. It can be sufficient if only those supply valves for supply fluid lines that convey particularly sensitive fluids are embodied to be switchable by the switching device. The number of supply switching locations can thus be smaller than the number of supply valves. What is of paramount importance is the simultaneous switchability of supply valves. For example, it can be theoretically conceivable for a magnet to be displaceable in such a way that at a first point in time it interacts with a first supply switching location for switching a first supply valve, and at a later second point in time it interacts with a second supply switching location, different therefrom, for switching a second supply valve. The first and the second supply valve are consequently not switchable simultaneously. This instance as well is consistent with the definition above that the number of supply switching locations is smaller than the number of supply valves.

One supply switching location is associated with one supply valve, and as a rule is therefore stationary with respect to the fluid conduit and/or to a housing of the fluid supply interface.

Advantageously, the at least one discharge valve can also be switchable by the switching device between its operating positions irrespective of the fluid pressure existing at the at least one discharge valve.

It can furthermore be necessary, in order to manage several cell culture containers, to convey different fluids out of the fluid conduit or out of the respectively coupled-on cell culture container. It is possible for that purpose to provide a plurality of discharge coupling configurations that are connected to one another by the fluid conduit and each comprise a discharge valve, such that an external magnetic field generated by the at least one magnet is modifiable by the switching device at a discharge switching location so that a discharge valve provided at the discharge switching location can be switched between its operating positions. The number of discharge switching locations is the same as or smaller than the number of discharge valves. The statements made above with regard to the plurality of supply valves and their interaction with the switching device apply correspondingly here to the at least one discharge valve and its interaction with the switching device.

In order always to reduce an overpressure deliberately via the same fluid line, and thereby to avoid undesired contamination of a further discharge fluid line used for overpressure reduction in the fluid conduit, preferably only exactly one discharge valve of the fluid supply interface is embodied as a safety valve as described above in conjunction with achieving the object on which the present invention is based. All further discharge valves are preferably constructed in terms of design like the supply valves, and merely have, during operation, a function that deviates from them, namely a function serving at least predominantly to convey fluids out of the fluid conduit. With these further discharge valves, however, the valve body preferably lifts off toward the fluid conduit in order to switch the discharge valve into the flowthrough position, and not (as is the case with the safety valve switchable by means of a pressure difference) preferably away from the fluid conduit. The statements made above with regard to the at least one supply valve therefore correspondingly apply mutatis mutandis to the at least one further discharge valve present in addition to the safety valve, also and in particular in conjunction with the retaining configuration for ensuring that the valve body remains on the respective valve. A retaining configuration as described above is therefore preferably also provided for one or several further discharge valves on the fluid supply interface.

The at least one further discharge valve, like the at least one further supply valve, also preferably comprises a magnetic preloading device in order to preload the valve body into the closed position.

Preferably the spacing of a discharge valve and a supply valve from one another in a longitudinal direction of the fluid conduit is greater than the spacing in the same direction between two discharge valves and/or between two supply valves. As a result, the user coupling configuration can be arranged between a discharge valve and a supply valve, and can be influenced by an external magnetic field, with no risk that the magnetic field acting at the location of the user coupling configuration, i.e. at a user switching location, might undesirably also act on a supply valve or a discharge valve and unintentionally bring about a switchover of the operating position there.

In accordance with what has been said above, in a refinement of the fluid supply interface according to the present invention provision can be made that an external magnetic field generated by a magnet is also modifiable by the switching device at a user switching location that is located in the region of the user coupling configuration and at which a user fluid line having a user valve can temporarily be arranged, so that the user valve provided at the user switching location can be switched between its operating positions (locked position and flowthrough position). In the case in which a plurality of user coupling configurations are provided, exactly as many user switching locations as user coupling configurations are preferably provided, in order to ensure that each user valve temporarily arranged at a user coupling configuration is switchable independently of the respective other user valve.

In a cell culture management system using the fluid supply interface according to the present invention, a supply coupling configuration is preferably coupled by means of a supply fluid line to a cleaning fluid reservoir in order to enable thorough cleaning of the fluid supply interface between two coupling operations of different cell culture containers. The risk of cross-contamination between multiple cell culture containers can thereby be reduced or even excluded.

In order to allow cleaning of the fluid supply interface to be performed as thoroughly as possible, according to a refinement of the present invention the fluid supply interface can be coupled to a backwash apparatus by means of which a given fluid is drivable to flow in opposite directions in the fluid conduit. The fluid conduit can thus, for example, be filled with cleaning fluid, and the cleaning fluid column present in the fluid conduit can then be moved in opposite directions so as to achieve, in addition to the chemical cleaning effect due to the fluid composition, a mechanical cleaning effect as a result of the fluid motion, specifically avoiding any flow "shadow" regions into which a cleaning fluid would flow insufficiently if flow occurred in only one direction of motion.

The cleaning fluid is, however, only an example. The use of the backwash apparatus is not intended to be limited thereto. For example, it can also be advantageous to use the backwash apparatus in conjunction with other fluids, for example to bring about maximally complete wetting of the fluid conduit and of all valve bodies possibly projecting into it, before that fluid or another fluid is conveyed into or out of a cell culture container.

In order to achieve the aforesaid backwash effect, it is advantageous if the backwash apparatus encompasses a reversible-direction pump. The latter can be a continuously operating reversible-rotation-direction pump or it can be a piston-cylinder arrangement, the latter being preferred because of the precise fluid motion that is achieved. The piston can be drivable, for example, by a rotating eccentric drive to move back and forth in the cylinder, moving the liquid column present in the fluid conduit in one or the other, opposite, direction depending on the piston motion that is respectively present.

In order to allow the backwash apparatus to be separated in terms of action from the fluid conduit if desired, provision can be made that a backwash fluid line that connects the reversible-direction pump to the fluid conduit is provided upstream, in a supply flow direction or delivery flow direction from the supply coupling configuration to the user coupling configuration, from the supply valve.

The present invention further relates to use of a fluid supply interface, as described and refined above, to manage cell culture containers on which at least one counterpart user coupling configuration is respectively provided for temporary coupling to the at least one user coupling configuration.

The present invention further relates to a cell culture management system having a fluid reservoir, having a discharge sink, and having a fluid supply interface as described and refined above. The fluid reservoir is coupled via a supply fluid line to the supply coupling configuration, the discharge sink is coupled via a discharge fluid line to the discharge coupling configuration, and a cell culture container is detachably couplable onto the at least one user coupling configuration.

A cell culture container, or a plurality of cell culture containers, does not need to be part of the cell culture management system but preferably is a constituent thereof.

A fluid reservoir can encompass a container having a supply of fluid or, for example in the case of tap water, can encompass a fluid-carrying supply line.

The discharge sink can likewise encompass a container in which fluid discharged from a cell culture container is collected. This is the case in particular when the fluid conveyed out of the cell culture container is the desired result of cell culturing. Alternatively, the discharge sink can be a piping system, for example a wastewater system or waste disposal system of a local authority in which the cell culture management system is being operated.

In order also to bring about with the backwash apparatus a fluid motion at the valve that selectably admits or blocks the backwashing fluid, it is advantageous if the backwash fluid line connects into the supply fluid line upstream, in a supply flow direction or delivery flow direction from the supply coupling configuration to the user coupling configuration, from the supply valve.

It can furthermore be desirable for the backwash apparatus, when it is performing a backwashing operation, to have no feedback into the fluid reservoir which is coupled to the same supply coupling configuration as the backwash apparatus and in which high-purity fluid as a rule is furnished. Provision is therefore made in accordance with a further preferred refinement of the present invention that a shutoff valve is provided upstream, in a supply flow direction or delivery flow direction from the supply coupling configuration to the user coupling configuration, from the connection of the backwash fluid line into the supply fluid line, by way of which valve a portion of the supply fluid line located upstream from the connection point is disconnectable from the backwash fluid line.

Also to be noted is the fact that the indication of a flow direction from one point to another point in a fluid line not only relates to the flow state between the aforesaid points but also indicates a flow direction that applies to every point in a fluid line that is in fluid-conveying communication with the aforesaid points in terms of fluid mechanics.

In order to allow cell cultures in the cell culture containers to be managed as comprehensively as possible by way of the cell culture management system presented here, the cell culture management system comprises a cleaning fluid reservoir constituting the aforementioned fluid reservoir, and additionally comprises a nutrient medium reservoir constituting a further fluid reservoir. The cell culture management system furthermore preferably additionally comprises a harvest sink, constituting a further sink, into which fluid is conveyed out of a cell culture container coupled onto the fluid supply interface so that completely cultured cell cultures can be harvested and further processed as intended.

The cleaning fluid reservoir is then coupled via a first supply fluid line to a first supply coupling configuration, the first supply fluid line preferably being the supply fluid line into which the backwash fluid line connects as described above.

The at least one nutrient medium reservoir is likewise coupled via a second supply fluid line to a second supply coupling configuration.

The cell culture management system can furthermore comprise one or several functional fluid reservoirs, for example for furnishing a flushing fluid in order to clean nutrient medium off adherent cells in the cell culture container and/or in order to furnish a detachment fluid for detaching adherent cells from their substrate surfaces in the cell culture container. These functional fluid reservoirs can be coupled via third and even further supply fluid lines to third and even further supply coupling configurations.

The discharge sink is coupled via a first discharge fluid line to a first discharge coupling configuration. The discharge sink serves as what is often referred to as a "waste" sink, for final disposal of fluid conveyed out of cell culture containers coupled to the supply interface and/or out of the supply interface itself.

The harvest sink is preferably coupled via a second discharge fluid line to a second discharge coupling configuration.

Preferably the discharge coupling configuration coupled to the discharge sink, particularly preferably only the discharge coupling configuration coupled to the discharge sink, comprises the aforementioned discharge valve that is embodied as a safety valve and opens in the context of a predetermined pressure difference, which enables overpressure reduction in the fluid conduit via an outflow of fluid from of the fluid conduit to the discharge sink.

Also preferably, the harvest coupling configuration is embodied as a discharge configuration for conveying fluid out of a cell culture container or out of the fluid supply interface, but is configured physically like a supply coupling configuration. Of the two aforesaid discharge valves, preferably each one is switchable between its operating positions by the switching device. The discharge valve associated with the harvest sink, however, in contrast to that of the first discharge coupling configuration, cannot be opened by an overpressure in the fluid conduit with respect to a fluid pressure in the second discharge fluid line.

If applicable, the discharge valve associated with the discharge sink and embodied as a safety valve can be openable exclusively by way of a fluid overpressure.

Of the supply valves, preferably only the one of the first supply line coupled to the cleaning fluid reservoir is switchable by the switching device. For the second and each further supply fluid line, it can be sufficient if they are openable by way of an overpressure in the respective supply fluid line with respect to a fluid pressure present in the fluid conduit.

For example, a third supply coupling configuration can be provided, which is coupled via a third supply fluid line to a washing fluid reservoir for cleaning nutrient medium off cultured cells.

A fourth supply coupling configuration can also be provided, which is coupled via a fourth supply fluid line to a reservoir of trypsin-EDTA, so that detachment of adherent cells from an inner wall of a cell culture container coupled onto the fluid supply interface can be brought about.

With the exception of the aforesaid first discharge coupling configuration, all the coupling configurations, including the valves provided with them, are preferably physically identical. In order to facilitate coupling of a cell culture container, on the one hand the at least one supply coupling configuration and the at least one discharge coupling configuration, and the user coupling configuration, are located with respect to the fluid conduit on different sides of the fluid supply interface.

The cell culture management system can encompass at least one pump in order to deliberately generate an overpressure (as a rule in a supply fluid line) or a negative pressure (as a rule in a discharge line) in a fluid line.

Preferably only one fluid line is connected to each pump, so that cross-contamination can be avoided here as well. The provision of pumps is, however, not absolutely necessary. On the one hand, a fluid reservoir can be at an overpressure, or a sink at a negative pressure, with reference to atmospheric pressure. By way of suitable control valves, the overpressure present in a respective reservoir or the negative pressure present in the respective sink can then be coupled into the connected fluid line. On the other hand, at least one fluid reservoir can be arranged in elevated fashion oppositely to the direction of gravity with respect to the fluid supply interface and the cell culture containers coupled thereto, so that a hydrostatic pressure difference is established between the fluid reservoir and fluid conduit as a result of the difference in elevation between the fluid reservoir and fluid conduit. Here as well, the hydrostatic overpressure that is generated in a supply fluid line to a fluid reservoir can be exerted, or not, on the respective connected supply valve by way of suitable control valves.

The present invention will be explained in further detail below with reference to the appended drawings, in which.

Figure 1:
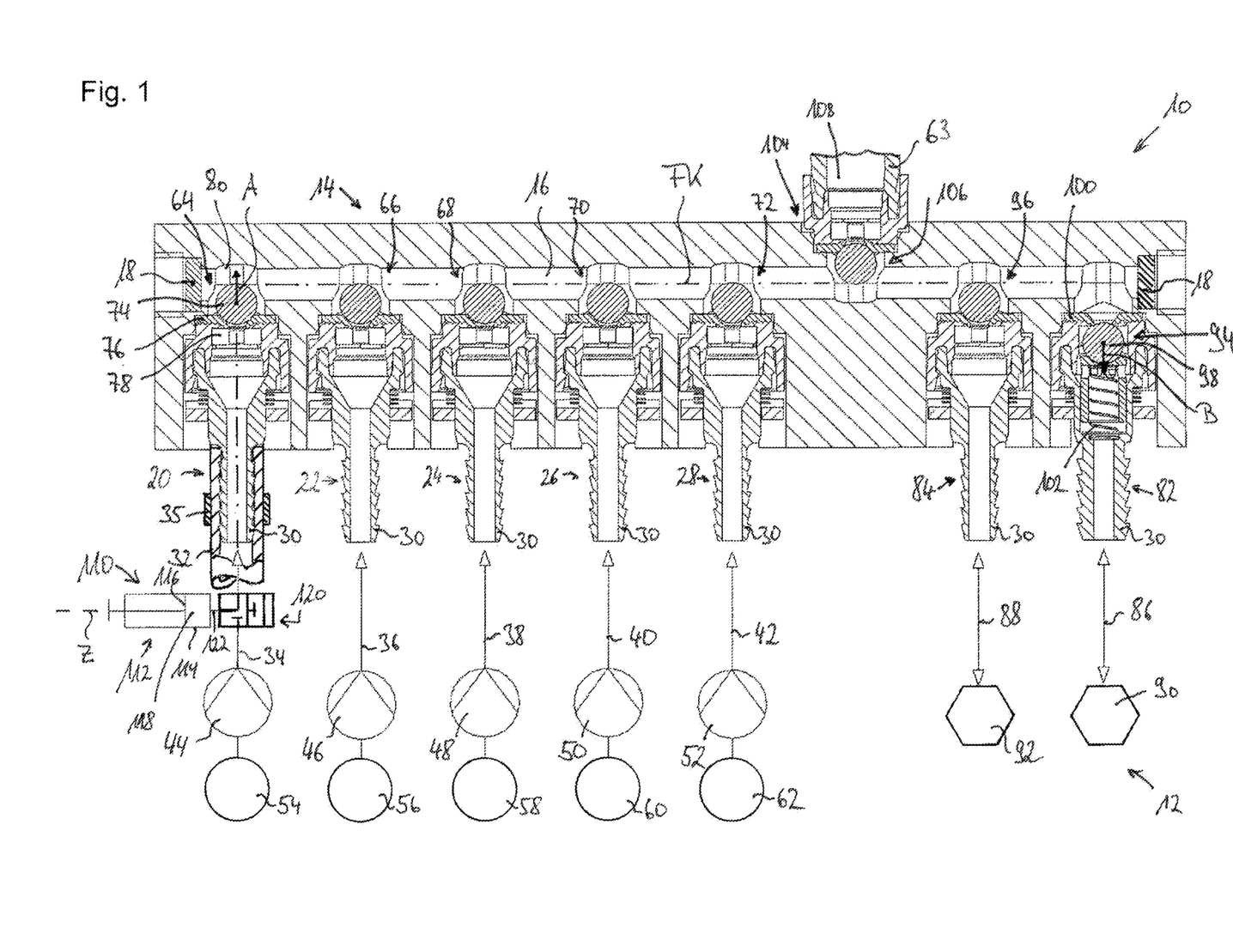
FIG. 1 is a schematic and in part highly schematic section view through a fluid supply interface according to the present invention of a cell culture management system also in accordance with the present invention.

In FIG. 1, a fluid interface according to the present invention is labeled in general with the number 10. It is part of a cell culture management system 12.

In the example depicted, fluid supply interface 10 has a preferably one-piece housing 14 that is penetrated in a longitudinal direction by a fluid conduit 16 that extends preferably along a straight-line fluid conduit axis FK. Fluid conduit 16, preferably manufactured as a through bore, is closed off at its two longitudinal ends by a respective stopper 18.

In the example depicted, fluid supply interface 10 comprises five supply coupling configurations that are referred to hereinafter as first to fifth supply coupling configurations 20, 22, 24, 26, and 28. Supply coupling configurations 20 to 28 are preferably embodied identically, and for that reason only first supply coupling configuration 20 will be described hereinafter as a representative of all supply coupling configurations 20 to 28.

Supply coupling configurations 20 to 28 can comprise, for example, a tube fitting 30 onto which a hose 32 of a supply fluid line 34 can be slid and can be secured, for example by way of a hose clamp 35, against being unintentionally pulled off tube fitting 30. Tube fitting 30 can furthermore have barbs that make pulling off more difficult.

Each supply coupling configuration 20 to 28 has associated with it a supply fluid line 34 to 42 that respectively encompasses a hose and can thereby be coupled permanently (as defined in the present Application), in the manner described above, to the respective supply coupling configuration for fluid transfer. The supply fluid lines are referred to hereinafter using the same ordinal number as the supply coupling configuration to which they are connected, so that in the present example a first to fifth supply fluid line 34, 36, 38, 40, and 42 exist.

In the present example each supply fluid line 34 to 42 furthermore has associated with it a respective supply pump 44 to 52 that can elevate the fluid pressure in its respectively associated supply fluid line in order to convey the fluid flowing through the respective supply fluid line into fluid conduit 16. If necessary, supply pumps 44 to 52 are referred to hereinafter using the same ordinal number as the supply fluid lines associated with them, so that first to fifth supply pumps 44, 46, 48, 50, and 52 exist. Fluid flows through supply coupling configurations 20 to 28, as intended, in a supply direction toward fluid conduit 16.

In addition, each supply fluid line 34 to 42 is connected to a fluid reservoir 54 to 62 from which fluid can be conveyed via supply pumps 44 to 52 to fluid conduit 16.

For example, first fluid reservoir 54 can be a cleaning fluid reservoir in which water, or a cleaning agent specifically matched to the respective culturing instance, or air, can be stored.

A nutrient medium having nutrients for the cells to be cultured in cell culture container 63 can be stored, for example, in second fluid reservoir 56.

A cleaning liquid, for example phosphate-buffered salt (PBS) solution, with which nutrient medium adhering to cells of a cell culture can be cleaned off them, can be stored, for example, in third fluid reservoir 58.

A medium for detaching adherent cells from their surface substrate to which they are adhering can be stored, for example, in fourth fluid reservoir 60. One such medium is, for example, trypsin-EDTA.

Fifth fluid reservoir 62 can store a reserve nutrient medium in order to ensure an uninterrupted supply of nutrient medium to cell cultures. The occupancy of fluid reservoirs 54 to 62 can, however, of course also be different from the aforementioned example.

Supply coupling configuration 20, which can be embodied in one piece or in multiple parts, has a supply valve 64 at its longitudinal end located closer to fluid conduit 16. Fluid supply interface 10 comprises a first to a fifth supply valve 64, 66, 68, 70, and 72 so that as a function of the latter's operating position, each supply fluid line 34 to 42 either is blocked for fluid flow or is open for flow by way of a respective supply valve.

First supply valve 64 will be described below as an example of all the further identically constructed supply valves 66 to 72. First supply valve 64 comprises a spherical valve body 74 that is manufactured from ferromagnetic but not magnetized material. When supply valve 64 is in the blocking position, this spherical valve body 74 rests on a flexible valve seat, made e.g. of silicon elastomer, against which valve body 74 sealingly abuts in its blocking position, accompanied by slight deformation of valve seat 76. Valve body 74 is magnetically preloaded into its blocking position, shown in FIG. 1, by means of an annular permanent magnet 78 through which fluid can flow in its central passage.

In the blocking position, valve body 74 preferably projects over no more than half its diameter into fluid conduit 16.

For transition into its passthrough position in which first supply valve 64 allows passage of a fluid flow from first fluid reservoir 54 to fluid conduit 16, valve body 74 is moved in a lifting direction A preferably orthogonal to proceeding axis FK of fluid conduit 16. It is not to be excluded, however, that valve body 74 executes, in addition to a motion in lifting direction A, a slight sideways motion orthogonally to lifting direction A. This lateral motion is, however, not important. A switchover of the operating position of first supply valve 64, and of all further supply valves 66 to 72, always occurs when valve body 74 is moved away in lifting direction A off valve seat 76.

Fluid conduit 16 is preferably embodied, between two adjacent supply valves or in general between two adjacent valves, with a diameter that is less than the diameter of valve body 74, in order to prevent valve body 74 from being detached by the flow that is permitted by it—or, in the case of valves 76 to 72 located farther downstream, by a valve located upstream from it—and being no longer capable of being displaced back onto valve seat 76 into its blocking position.

In order to further assist retention of valve body 74 in its passthrough position in the vicinity of preload magnet 78, a retaining configuration 80 can be provided, which configuration is embodied, for example, directly as a configuration of the wall in housing 14 which encloses fluid conduit 16. For example, retaining formation 80 can be embodied opposite preload magnet 78 in lifting direction A as a concave wall configuration with respect to and within the cylindrical wall of fluid conduit 16. Whereas the cylindrical wall of fluid conduit 16 is curved only around proceeding axis FK of fluid conduit 16, retaining configuration 80 can additionally be curved around a curvature axis orthogonal both to fluid conduit axis FK and to lifting direction A. Retaining configuration 80 can then constitute a conforming surface for valve body 74 against which it abuts in its passthrough position.

In the present example, fluid supply interface 10 according to the present invention furthermore comprises a first discharge coupling configuration 82 and a second discharge coupling configuration 84.

Although flow can occur through discharge coupling configurations 82 and 84 in opposite directions, flow occurs through them predominantly, or in fact exclusively, in a discharge direction away from fluid conduit 16 when fluid supply interface 10 is in use as intended. Discharge coupling configurations 82 and 84, like supply coupling configurations 20 to 28, are embodied for the coupling of hoses of discharge fluid lines 86 and 88.

First discharge coupling configuration 82 is connected via first discharge fluid line 86 to a first discharge sink 90 in the form of a waste container. Discharge fluid line 86 thus constitutes a so-called "waste" line. Any intermediate product or final product of cell culturing which is discarded is delivered via first discharge fluid line 86 to waste container 90. In order to bring about the fluid flow in a discharge direction, waste container 90 can be at a relative negative pressure, or a delivery pump can be provided in discharge line 86 between discharge coupling configuration 82 and waste container 90.

Second discharge coupling configuration 84 is coupled via second discharge fluid line 88 to a harvest container 92 into which completely cultured cell cultures can be conveyed out of cell culture container 63 (depicted only in rudimentary fashion). Here as well, harvest container 92 can be under a relative negative pressure, or a delivery pump can be arranged in second discharge fluid line 88 in order to bring about a fluid flow in a discharge direction.

First discharge fluid line 86 can be closed off to prevent flow, or enabled for flow, by way of a first discharge valve arranged in fluid supply interface 10. Second supply fluid line 88 can be closed off or enabled for flow by way of a second discharge valve 96.

In the present example, second discharge coupling configuration 84 having second discharge valve 96 is constructed identically to first to fifth supply coupling configurations 20 to 28 having their first to fifth supply valves 64 to 72, so for a description of second discharge coupling configuration 84 having second discharge valve 96, reference is made to the description above of the supply coupling configurations having the supply valves.

First discharge valve 94, on the other hand, unlike all the discharge valves hitherto described, is constructed as a safety valve. It encompasses a ferromagnetic, but preferably not permanently magnetized, valve body 98 that, in its closed position shown in FIG. 1, abuts sealingly against a valve seat 100 constituted from flexible elastomeric material. Valve body 98 is preferably identical to valve bodies 74 of the remaining valves 64 to 72 and 96. Valve body 98, however, is preloaded into the closed position shown in FIG. 1 not by magnetic force but by means of a helical compression spring 102. The force necessary for displacing valve body 98 into its flowthrough position can be adjusted very precisely in terms of design by selection of a suitable spring steel or in general a suitable spring metal, by way of the dimensioning thereof (spring cross section), and by way of the dimensioning of preload spring 102 itself.

Helical compression spring 102 is preferred as a preload spring, since it allows valve body 98 to be acted upon by a preload force proceeding approximately through its center point and at the same time allows fluid to flow through it. Helical compression spring 102 is arranged in such a way that fluid in first discharge fluid line 86 can flow radially inward past the turns of helical compression screw 102. Valve body 98 of first discharge valve 94 could additionally or alternatively be preloaded into the closed position by magnetic force, but preloading exclusively with mechanical spring means is preferred.

In order to shift valve body 98 from the closed position depicted in FIG. 1 into its flowthrough position lifted off from valve seat 100, valve body 98 is movable in an opening direction B that is directed oppositely to lifting direction A of the remaining valve bodies in the example depicted. Both lifting direction A and opening direction B are preferably collinear with the direction in which the respective fluid lines 34 to 42, 86, and 88 proceed in the region of their coupling to fluid interface 10.

Because it is constituted from ferromagnetic material, valve body 98 of first discharge valve 94 can in principle be switched from the closed position shown in FIG. 1 into its flowthrough position by means of a change in an external magnetic field, i.e. by magnetic force. The switching magnet and preload spring 102 must be coordinated with one another for that purpose in such a way that the force exerted on valve body 98 by the switching magnet in the active switching state overcomes the force of the Hooke-type preload spring 102.

In the present example, supply coupling configurations 20 to 28 and discharge coupling configurations 82 and 84 each constitute a block of coupling configurations in which only functionally similar coupling configurations—supply coupling configurations on the one hand and discharge coupling configurations on the other hand—are arranged. The spacing along fluid conduit axis FK between the only adjacent coupling configurations 28 and 84 that (in the example depicted) have different functions is greater than between two supply coupling configurations 20 to 28 on the one hand, and discharge coupling configurations 82 and 84 on the other hand, that are directly adjacent in the same direction.

Tube fittings 30 of coupling configurations 20 to 28, 82, and 84 are preferably parallel to one another and are all located on the same side with respect to fluid conduit 16.

In the region between coupling configurations 28 and 84, the greater spacing between them is used in order to constitute a user coupling configuration 104. In order to facilitate the coupling of users, for example cell culture containers 63, thereonto, user coupling configuration 104 opens with respect to fluid conduit 16 onto a different side, preferably an opposite side, from coupling configurations 20 to 28, 82, and 84.

In FIGS. 1 to 5, a cell culture container 63 is shown coupled onto user coupling configuration 104. Said container comprises a user valve 106 that is embodied identically to supply valves 64 to 72 and to second discharge valve 96. Unlike supply valves 64 to 72 and discharge valve 96, however, user valve 106 is arranged not in stationary fashion on fluid supply interface 10, but instead in stationary fashion on cell culture container 63. A user fluid line 108 connects user valve 106 to a cell culture container body that is not completely depicted in FIGS. 1 to 5 but is known in principle to one skilled in the art.

Fluid supply interface 10 is furthermore coupled to a backwash apparatus 110 that is connected, in the example depicted, to further supply fluid line 34 through which cleaning fluid can be conveyed into fluid conduit 16. Backwash apparatus 110, which will be discussed below in further detail, encompasses in the example depicted a piston-cylinder arrangement 112 having a piston 116 movable in a cylinder 114 along the latter's cylinder axis Z. A volume 118 of backwash apparatus 110 connected to first supply fluid line 34 is thereby modifiable.

Backwash apparatus 110 is connected to first supply fluid line 34 via a shutoff valve 120 that is shiftable between a position in which only backwash apparatus 110 is connected in fluid-transferring fashion to first supply coupling configuration 20 and a position in which only first fluid reservoir 54 is connected fluid-transferringly to first supply coupling configuration 20.

Shutoff valve 120 can be preloaded into one of its two positions, preferably into the position in which first fluid reservoir 54 is coupled in fluid-transferring fashion to first supply coupling configuration 20.

Instead of the multi-position multi-path valve of FIG. 1, however, shutoff valve 120 can alternatively be constituted by a check valve of simpler construction that permits a fluid flow only in a direction from first fluid reservoir 54 to first supply coupling configuration 20, and blocks it in the opposite direction. In this case the alternative shutoff valve 120' is arranged upstream, in the only possible flow direction, from a connection point, then set up permanently, of a connecting line 122 into first supply fluid line 34. This alternative is depicted in FIG. 2.

Feedback of the operation of backwash apparatus 110 into first fluid reservoir 54, or in general into a portion of first supply fluid line 34 located between shutoff valve 120 or 120' and first fluid reservoir 54, can be prevented by shutoff valve 120 or 120'.

Figure 2:
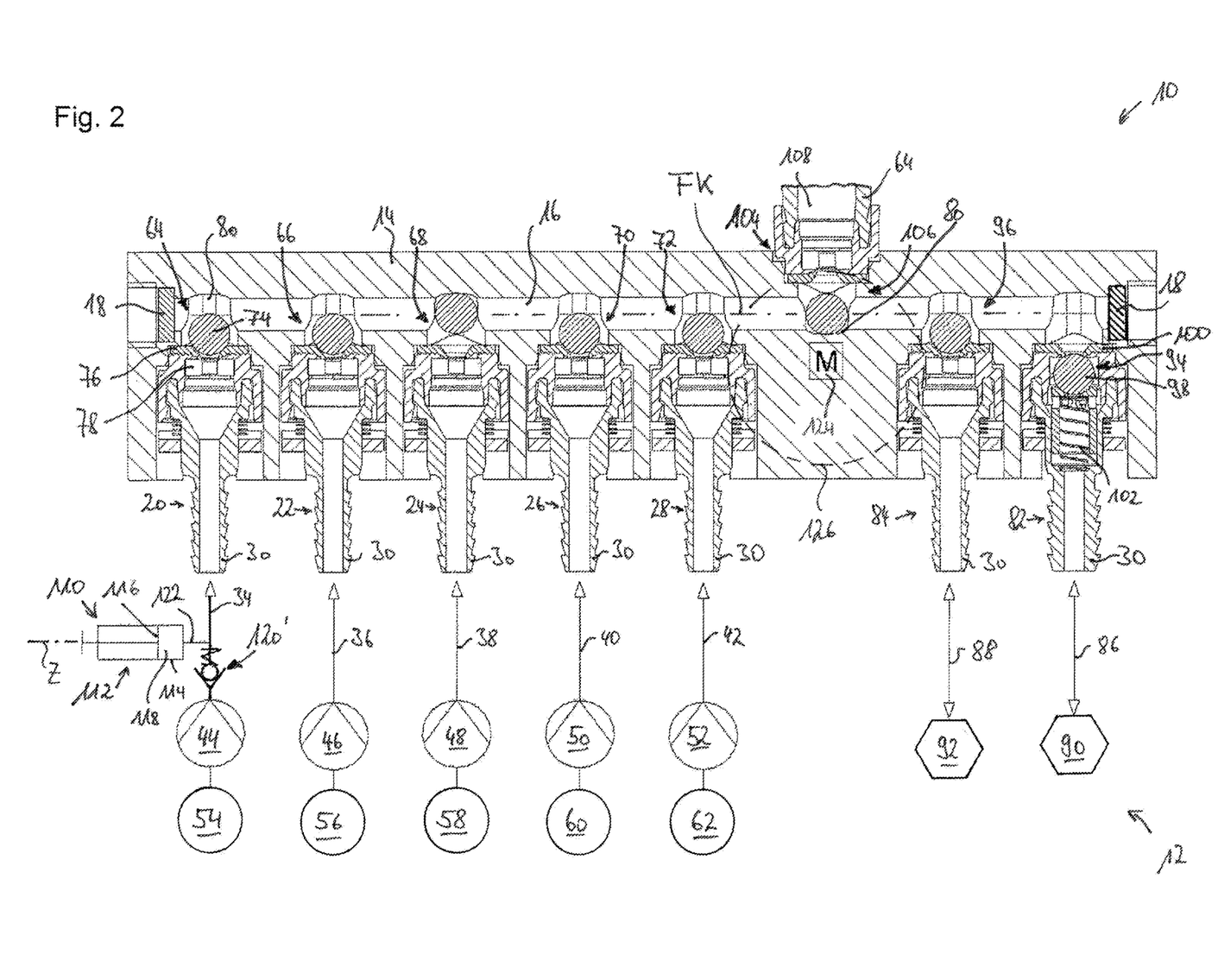
FIG. 2 is the view of FIG. 1 with a supply valve open and a user valve also open.

FIG. 2 depicts what is shown in FIG. 1, the operating position of third supply valve 68 and of user valve 106 having been modified.

User valve 106 has been switched into its passthrough position by a switching magnet 124 of a switching device. In the region of user coupling configuration 104 as well, a concave, if applicable cap-shaped, retaining configuration 80 of substantially similar type is embodied on the wall of fluid conduit 16 in order to retain the valve body of user valve 106, which is otherwise preferably identical to the remaining valve bodies, in the vicinity of the preload magnet that preloads it into its locked position. In the example depicted, user valve 106 is constructed identically to supply valves 64 to 72 and to second discharge valve 96, so that for a description thereof, reference is made to the description above of first supply valve 64.

Whereas in the present invention user valve 106 is always switched by switching magnet 124 of the switching device into its flowthrough position, shown in FIG. 2, in order to deliver fluid into cell culture container 63, the valve body of third supply valve 68, for example, is opened only by activation of pump 48 and, as a result of the pressure elevation thereby occurring in the fluid in third fluid line 38, as a result of the pressure difference that is established between the side closer to the pump, and the side closer to the fluid conduit, of the third supply valve. The elevated pressure on the side of third supply pump 48 moves the valve body of third supply valve 68 away from the valve seat until the valve body comes into abutment, for example, in retaining configuration 80 that is located opposite the valve seat in lifting direction A. Fluid can then be introduced from third fluid reservoir 58 through third supply fluid line 38, past third supply valve 68, through a portion of fluid conduit 16, past user valve 106 of cell culture container 63 that has just been coupled on, through user fluid line 108 into cell culture container 63.

In the present instance, for example, a completely cultured cell culture container 63 is being rinsed with PBS in order to remove nutrient media residues from the adherent cells still present in cell culture container 63.

Switching magnet 124 can be an electromagnet through which current flows or does not flow, as required. In the present example, switching magnet 124 is a permanent magnet 124 that can be brought closer to and farther from housing 14, and which in contrast to an electromagnet does not represent a heat source. In FIG. 2, dashed lines surround the region 126 that, constituting user switching location 126, indicates the region of influence of switching magnet 124.

By bringing switching magnet 124 close to housing 14 of fluid supply interface 10 it is possible to generate in user switching location 126 a magnetic field that is sufficiently strong to displace the valve body of user valve 106, against the action of its preload magnet in user valve 106, from its locked position into the flowthrough position shown in FIG. 2. When switching magnet 124 is moved back away from housing 14, the magnetic field that proceeds from switching magnet 124 and acts in switching location 126 becomes so greatly attenuated that the attractive force of the preload magnet in user valve 106 on the valve body of user valve 106 predominates, and displaces valve body 106 back into the locked position shown in FIG. 1.

Figure 3:
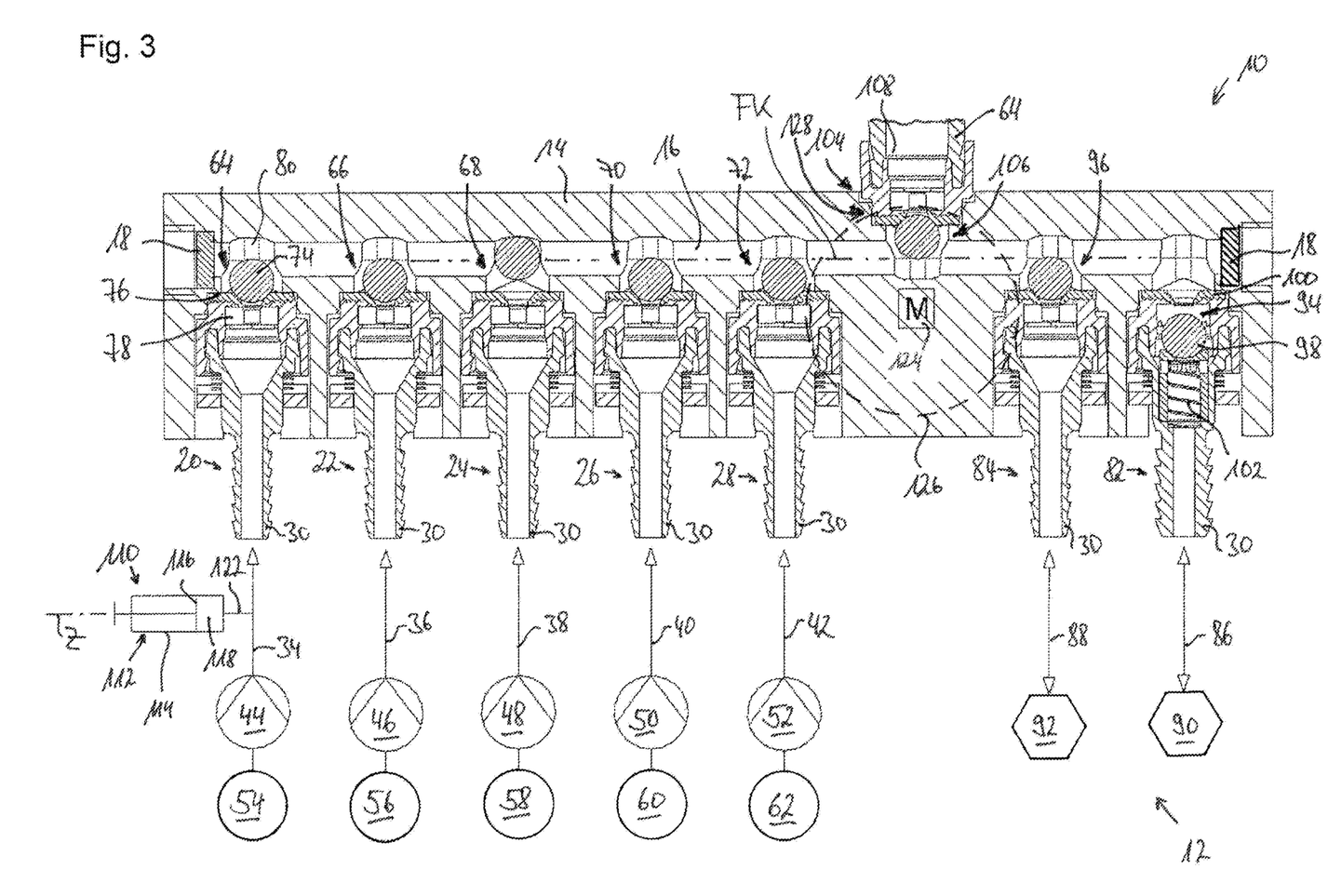
FIG. 3 is the view of FIG. 2, a discharge valve being opened, by overpressure in the fluid conduit, in place of a user valve that has erroneously not opened.

FIG. 3 shows the situation of FIG. 2, user valve 106 having erroneously not been displaced into the flowthrough position even though switching magnet 124 was brought closer to housing 14 and thus to user switching location 126. This fault can have a variety of causes, but they are not important in the present instance. Switching magnet 124 may have experienced a jam, and therefore possibly can be brought only insufficiently close to housing 14. It is likewise possible for unusually large clamping forces to have occurred between the valve body and the elastomeric material of the valve seat of user valve 106, so that the force exerted by switching magnet 124 is insufficient. Lastly, switching magnet 124 may have suffered a loss of magnetization due to the effect of an external magnetic field.

In any event, when third supply pump 48 is activated but user valve 106 is not in its flowthrough position, the pressure in fluid conduit 66 will rise to an undesirable extent. In the absence of further actions, it can happen that the fluid conveyed out of the third fluid reservoir breaks through at the seal formed by the material of the valve seat of user valve 106 between counterpart user coupling configuration 128 and user configuration 104 of supply fluid interface 10, emerges along the gap present between user coupling configuration 104 and counterpart user coupling configuration 128, and contaminates the operating space of fluid supply interface 10 or cell culture management system 12 as a whole.

This will not happen with the present embodiment of fluid supply interface 10, since in the context of a sufficiently increased pressure in fluid conduit 16, and thus a sufficiently large pressure difference between the fluid conduit side and the discharge sink side of first discharge valve 94, valve body 98 of first discharge valve 94 opens against the preload force of helical compression spring 102 and is displaced into the flowthrough position. As the operation of third supply pump 48 continues, fluid is then conveyed out of third fluid reservoir 58 directly into discharge sink 90. A dangerously large pressure buildup does not, however, occur in fluid conduit 16.

Figure 4:
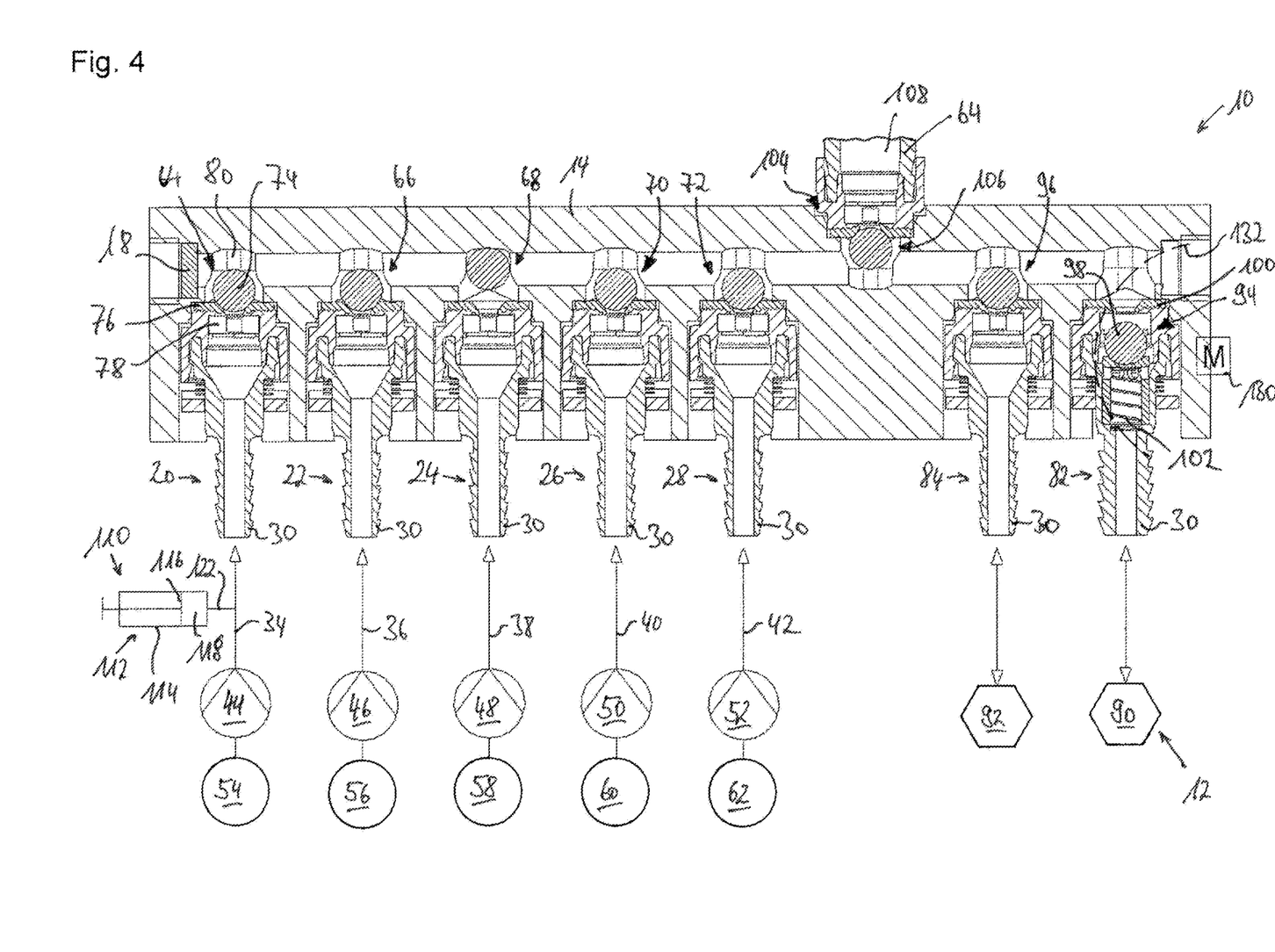
FIG. 4 is the view of FIG. 3 in which the discharge valve is switched into a flowthrough position by the magnet of a switching device.

FIG. 4 shows the same situation as in FIG. 3 but, as intended, user valve 106 is in its locked position and first discharge valve 94 has been displaced deliberately into the flowthrough position by bringing a second switching magnet 130 close to discharge switching location 132 associated with first discharge valve 94. The force of switching magnet 130 thus acts on valve body 98 of first discharge valve 94 to overcome the preload force of helical compression spring 102. This allows fluid conduit 16 to be flushed, in its portion between third supply valve 68 and first discharge valve 94, with the fluid present in third fluid reservoir 58 before that fluid is introduced into cell culture container 63.

Because of the nature of first discharge valve 94 as a mechanically preloaded overpressure valve, it would not necessarily require a switching actuation of first discharge valve 94 by means of switching magnet 130. The deliberate displacement of valve body 98 into the flowthrough position by means of switching magnet 130 of the switching device is nevertheless preferred over merely pushing first discharge valve 94 up by means of overpressure, since the valve operating position is then specified in defined fashion and is not influenced by the pressure and the spring feedback of helical spring 102.

Figure 5:
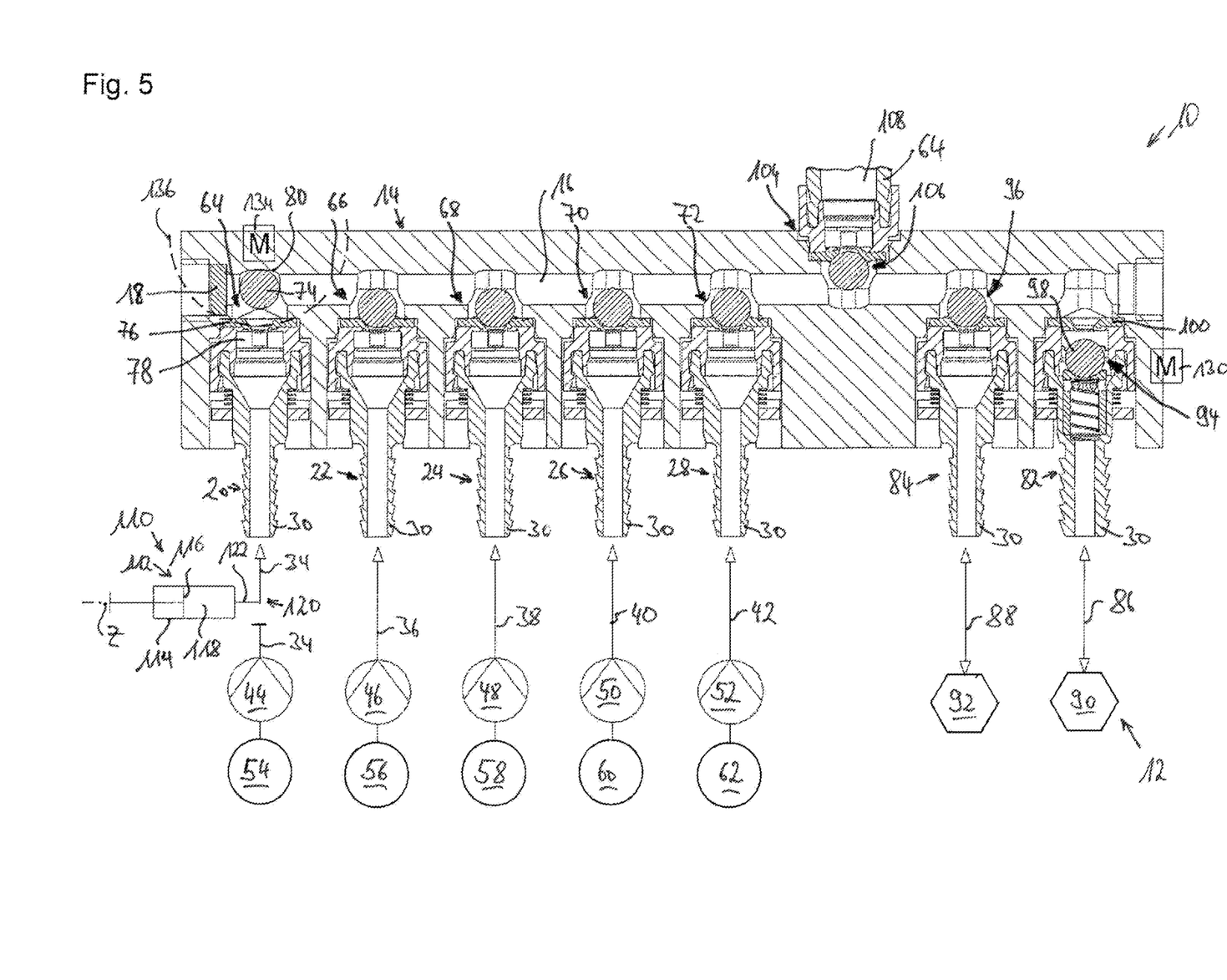
FIG. 5 is the view of FIGS. 1 to 4 with a further supply valve opened and with the discharge valve opened, each being shifted by a switching device into the passthrough or flowthrough position for cleaning with a backwash apparatus.

FIG. 5 depicts a situation in which first discharge valve 94 is displaced by switching magnet 130 into the flowthrough position, and in which valve body 74 of first supply valve 64 is displaced into the passthrough position by bringing a switching magnet 134 of the switching device closer in lifting direction A, accompanied by abutment against retaining configuration 80. Supply switching location 136, associated with first supply valve 64, of switching magnet 134 is drawn in with dashed lines.

This operating position of supply interface 10 serves for cleaning of fluid conduit 16 and of all the valve bodies projecting into it, including the valve body of a user valve 106 of a coupled-on cell culture container 63.

In order to achieve the longest possible cleaning path, preferably first supply coupling configuration 20 connected to cleaning fluid reservoir 54, and first discharge coupling configuration 82 connected to discharge sink 90, are arranged so that all the further valves and valve bodies of further coupling configurations are located between them. In the present example the spacing of first supply valve 64 from first discharge valve 94 is therefore the largest spacing existing in fluid supply interface 10 between valves of two coupling configurations that have different functions.

The conveying of cleaning fluid out of cleaning fluid reservoir 54 into discharge sink 90 usually produces sufficient cleaning of fluid conduit 16 and of all the valve constituents projecting into it.

This cleaning effect can be even further intensified by way of backwash apparatus 110.

In the situation shown in FIG. 5, fluid conduit 16 was firstly filled with cleaning fluid, whereupon shutoff valve 120 was actuated so that only backwash apparatus 110 is connected to fluid conduit 16, but first supply pump 44 no longer is. A back-and-forth motion of piston 16 in cylinder 114 thus allows the cleaning liquid conveyed into fluid conduit 16 to be moved in opposite directions through fluid conduit 16 and past all the valve constituents projecting into it. First supply valve 64 is completely rinsed by the back-and-forth motion of the cleaning fluid brought about by backwash apparatus 110.

The cleaning fluid thus has not only a chemical but also a mechanical cleaning effect, by the fact that it repeatedly flows in opposite directions past a given point of a component. At the end of such a backwash operation, backwash apparatus 110 can be disconnected again from fluid conduit 16 by shutoff valve 120 and lastly, clean cleaning fluid can be directed through fluid conduit 16 into discharge sink 90 by actuation of first supply pump 54. Thanks to shutoff valve 120, the cleaning fluid in first fluid reservoir 54 is not negatively affected by the backwash operation.

Piston 116 can be driven to move back and forth, for example, by a rotating eccentric drive. Other drive systems are also conceivable.

In the example depicted, of the valves shown on supply interface 10 only first supply valve 64, user valve 106, first discharge valve 94, and second discharge valve 96 are switchable between their operating positions by means of respective switching magnets 124, 130, and 134. The switching magnet for second discharge valve 96 is not depicted.

Second to fifth supply valves 66 to 72 are displaceable in pressure-induced fashion from their blocking position into the passthrough position exclusively by second to fifth supply pumps 46 to 52. Four switching magnets of a switching device are thus sufficient for the present fluid supply interface. It is thereby possible to prevent more than one valve body from being unintentionally moved by one switching magnet.

The invention claimed is:

1. A fluid supply interface for a cell culture system, the fluid supply interface comprising:
   at least one supply coupling configuration for receiving a respective supply fluid line;
   at least one discharge coupling configuration for receiving a respective discharge fluid line, different from the supply fluid line;
   at least one user coupling configuration for receiving a respective user fluid line, different from the supply fluid line and the discharge fluid line;
   a fluid conduit that connects the at least one supply coupling configuration, the at least one discharge coupling configuration, and the at least one user coupling configuration to one another;
   at least one supply valve by means of which, depending on an operation position of the at least one supply valve, a supply coupling configuration of the at least one supply coupling configuration is capable of having fluid flow therethrough or is blocked for flow therethrough;
   at least one discharge valve, different from the at least one supply valve, by means of which, depending on an operation position of the at least one discharge valve, a discharge coupling configuration of the at least one discharge coupling configuration is capable of having fluid flow therethrough or is blocked for flow therethrough; and
   a retaining configuration embodied in the fluid conduit;
   wherein the at least one supply valve being preloaded into a blocking position that prevents flow, and opening by means of a sufficiently large pressure difference between two sides of the at least one supply valve, against the preload force, for flow through in a direction from the at least one supply coupling configuration toward the fluid conduit, the at least one discharge valve likewise being preloaded into a closed position that prevents flow therethrough,
   wherein the at least one discharge valve, constituting a safety valve, is embodied to open upon exceedance of a predetermined pressure difference between the two sides of the safety valve, against its preload force, for flow through in a direction away from the fluid conduit and toward the at least one discharge coupling configuration,
   wherein, each of the at least one supply valve and the at least one discharge valve includes a valve body,
   wherein, when the valve body of the at least one supply valve and/or the at least one discharge valve is lifted off a valve seat, the retaining configuration retains the valve body of the at least one supply valve or the at least one discharge valve in an influence region of the preload force,
   wherein the at least one discharge valve and the at least one supply valve comprise the same valve bodies;
   wherein the flow cross section of the fluid conduit in a portion adjacent to the retaining configuration is smaller than a cross-sectional dimension of the valve body of the at least one supply valve and the valve body the at least one discharge valve orthogonally to the path along which the fluid conduit proceeds in the adjacent portion, so that penetration of the valve body of the at least one supply valve and the valve body the at least one discharge valve into the fluid conduit is prevented.

2. The fluid supply interface according to claim 1, wherein the safety valve comprises a mechanical preload device.

3. The fluid supply interface according to claim 1, wherein the valve body of the safety valve having or made of ferromagnetic and/or permanently magnetized material and is switchable between a closed position and a flowthrough position by modification of an external magnetic field, and/or the valve body of the at least one supply valve having or made of ferromagnetic and/or permanently magnetized material and is switchable between a blocking position and a passthrough position by modification of an external magnetic field.

4. The fluid supply interface according to claim 1, wherein the fluid conduit encloses an angle with the lifting direction of the valve body of the at least one supply valve and/or of at least one discharge valve.

5. The fluid supply interface according to claim 1, wherein the at least one supply coupling configuration comprises a plurality of supply coupling configurations, which
  are connected to one another by the fluid conduit, and each comprise a supply valve that
    is preloaded into a blocking position in which flow through the respective supply coupling configuration is prevented, and
    as a result of a sufficiently large pressure difference between the two sides of the supply valve, opens against the preload force for flow through in a direction from the respective supply coupling configuration toward the fluid conduit,
    wherein the fluid supply interface includes a switching device having at least one magnet with which, at a supply switching location, an eternal magnetic field generated by the at least one magnet is modifiable so that a supply valve of the one of the plurality of supply configurations provided at the supply switching location can be switched between its operation positions, a number of supply switching locations being smaller than the number of supply valves.

6. The fluid supply interface according to claim 5, wherein the at least one discharge valve is also switchable between its operating positions by the switching device.

7. The fluid supply interface according to claim 6, wherein the at least one discharge coupling configuration comprises a plurality of discharge coupling configurations that are connected to one another by the fluid conduit and each comprise a discharge valve of the one of the plurality of discharge coupling configuration are provided, such that an external magnetic field generated by the at least one magnet is modifiable by the switching device at a discharge switching location so that a discharge valve provided at the discharge switching locations being the same as or smaller than the number of discharge valves.

8. The fluid supply interface according to claim 5, wherein the external magnetic field generated by the at least one magnet is also modifiable by the switching device at a user switching location that is located in the region of the user coupling configuration and at which a user fluid line having a user valve can temporarily be arranged, so that the user valve provided at the user switching location can be switched between a locked position and a flowthrough position.

9. The fluid supply interface according to claim 1, wherein the fluid supply interface is coupled to a backwash apparatus by means of which a given fluid is drivable to flow in opposite directions in the fluid conduit.

10. The fluid supply interface according to claim 9, wherein the backwash apparatus encompasses a reversible-direction pump.

11. The fluid supply interface according to claim 10, wherein a backwash fluid line that connects the reversible-direction pump to the fluid conduit is provided upstream, in a delivery flow direction from the at least one supply coupling configuration to the at least one user coupling configuration, from the at least one supply valve.

12. A cell culture management system having a fluid reservoir, having a discharge sink, and having a fluid supply interface according to claim 1, wherein the fluid reservoir is coupled via a supply fluid line to the at least one supply coupling configuration, the discharge sink is coupled via a discharge fluid line to the at least one discharge coupling configuration, and a cell culture container is detachably coupled onto the at least one user coupling configuration.

13. The fluid supply interface according to claim 1, wherein the safety valve comprises a spring device.

14. The fluid supply interface according to claim 1, wherein the safety valve comprises a helical compression spring.

15. The fluid supply interface according to claim 1, wherein the valve bodies of the at least one discharge valve and the at least one supply valve comprise spherical valve bodies.

16. The fluid supply interface according to claim 1, wherein the retaining configuration is embodied in the fluid conduit as a wall configuration of the fluid conduit.

17. The fluid supply interface according to claim 4 wherein the angle is a right angle.

18. The fluid supply interface according to claim 9, wherein the backwash apparatus encompasses a reversible-direction pump having a piston-cylinder arrangement.

* * * * *